United States Patent [19]

Fischetti et al.

[11] Patent Number: 5,352,588
[45] Date of Patent: Oct. 4, 1994

[54] STREPTOCOCCAL IMMUNOGLOBULIN A BINDING PROTEIN ENCODED BY EMML2.2

[75] Inventors: Vincent A. Fischetti, West Hempstead; Debra E. Bessen, New York, both of N.Y.

[73] Assignee: Rockefeller University, New York, N.Y.

[21] Appl. No.: 813,584

[22] Filed: Dec. 24, 1991

[51] Int. Cl.⁵ .................. C07K 13/00; C12N 15/31; C12N 1/21
[52] U.S. Cl. ................... 435/69.1; 530/350; 536/23.7; 435/320.1; 435/252.3; 435/252.33
[58] Field of Search .............. 536/23.7; 530/350; 435/252.3, 252.33, 320.1, 69.1

[56] References Cited

U.S. PATENT DOCUMENTS 4,757,134 7/1988 Blake et al. .................. 530/350
5,210,183 5/1993 Lindahl et al. ................ 530/350

OTHER PUBLICATIONS

Bessen, D. E. et al. (1992) *Infect. Immun.* 60: 124–35.
Jeppson, H., et al. (1992) *FEMS Microbiol. Lett.* 92: 139–46.
Frithz, E., et al. (1989) *Mol. Microbiol.* 3: 1111–19.
Haanes, E. J., et al. (1989) *J. Bacteriol.* 171: 6397–6408.
Khandke, K. M., et al. (1988) *J. Biol. Chem.* 263: 5075–82.

*Primary Examiner*—Garnette D. Draper
*Assistant Examiner*—David L. Fitzgerald
*Attorney, Agent, or Firm*—Saliwanchik & Saliwanchik

[57] ABSTRACT

The subject invention concerns a novel polynucleotide sequence cloned from emm2.2 gene of a Group A streptococcus, Type II strain which codes for an IgA-binding protein, ML2.2. A process for producing the protein is given. The invention also concerns the protein in an immunoadsorbent and as a tracer for use in measuring and purifying IgA. Kits are given comprising the immunoadsorbent and the tracer form of the protein.

7 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1560 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 2..40

( i x ) FEATURE:
        ( A ) NAME/KEY: CDS
        ( B ) LOCATION: 252..1367

( x i ) SEQUENCE DESCRIPTION: SEQ ID NO:1:

```
A  TCT  GCA  GGT  ATG  CTT  GCT  CTA  AAA  CGC  AAA  GAA  GAA  AAC  TAAGCATTAG          50
   Ser  Ala  Gly  Met  Leu  Ala  Leu  Lys  Arg  Lys  Glu  Glu  Asn
   1              5                        10

ACTGATGCTA   AAGCTAAGAG   AGAATCAAAT   GATTCTCTCT   TTTGAGTGG    CTAAGTAACT       110

AACAATCTCA   GTTAGACCAA   AAAATGGGAA   TGGTTCAAAA   AGCTGGCCTT   TACTCCTTTT      170

GATTAACCAT   ATATAATAAA   AACATTAGGA   AAATAATAGT   AATATTAAGT   TTGTTTCCTC      230

AATAAAATCA   AGGAGTAGAT   A  ATG  GCT  AGA  CAA  CAA  ACC  AAG  AAA  AAT  TAT       281
```

|  |  |  |  |  |  | Met<br>1 | Ala | Arg | Gln | Gln<br>5 | Thr | Lys | Lys | Asn | Tyr<br>10 |  |
|---|---|---|---|---|---|---|---|---|---|---|---|---|---|---|---|---|
| TCA<br>Ser | CTA<br>Leu | CGA<br>Arg | AAA<br>Lys | CTA<br>Leu<br>15 | AAA<br>Lys | ACC<br>Thr | GGT<br>Gly | ACG<br>Thr | GCT<br>Ala<br>20 | TCA<br>Ser | GTA<br>Val | GCC<br>Ala | GTT<br>Val | GCT<br>Ala<br>25 | TTG<br>Leu | 329 |
| ACC<br>Thr | GTT<br>Val | TTG<br>Leu | GGC<br>Gly<br>30 | GCA<br>Ala | GGT<br>Gly | TTT<br>Phe | GCA<br>Ala | AAC<br>Asn<br>35 | CAA<br>Gln | ACA<br>Thr | GAA<br>Glu | GTA<br>Val | AGA<br>Arg<br>40 | GCT<br>Ala | GAT<br>Asp | 377 |
| GAA<br>Glu | GCT<br>Ala | AAA<br>Lys<br>45 | AAA<br>Lys | ATG<br>Met | GAA<br>Glu | GTA<br>Val | AAA<br>Lys<br>50 | GAA<br>Glu | AGT<br>Ser | GAA<br>Glu | AAA<br>Lys | GAG<br>Glu<br>55 | TCC<br>Ser | CAG<br>Gln | TAT<br>Tyr | 425 |
| AAG<br>Lys | ACG<br>Thr<br>60 | TTG<br>Leu | GCT<br>Ala | TTA<br>Leu | AGA<br>Arg | GGT<br>Gly<br>65 | GAA<br>Glu | AAT<br>Asn | GCT<br>Ala | GAC<br>Asp | CTT<br>Leu<br>70 | AGA<br>Arg | AAT<br>Asn | GTA<br>Val | AAT<br>Asn | 473 |
| GCA<br>Ala<br>75 | AAA<br>Lys | TAT<br>Tyr | TTA<br>Leu | GAG<br>Glu | AAA<br>Lys<br>80 | ATT<br>Ile | AAC<br>Asn | GCA<br>Ala | GAA<br>Glu | GAA<br>Glu<br>85 | GAA<br>Glu | AAA<br>Lys | AAT<br>Asn | AAA<br>Lys | AAG<br>Lys<br>90 | 521 |
| CTT<br>Leu | GAA<br>Glu | GCA<br>Ala | ATT<br>Ile | AAT<br>Asn<br>95 | AAA<br>Lys | GAG<br>Glu | CTA<br>Leu | AAT<br>Asn | GAG<br>Glu<br>100 | AAT<br>Asn | TAT<br>Tyr | TAC<br>Tyr | AAA<br>Lys | TTA<br>Leu<br>105 | CAG<br>Gln | 569 |
| GAT<br>Asp | GGC<br>Gly | ATT<br>Ile | GAT<br>Asp<br>110 | GCT<br>Ala | CTA<br>Leu | GAA<br>Glu | AAA<br>Lys | GAA<br>Glu<br>115 | AAA<br>Lys | GAA<br>Glu | GAT<br>Asp | CTC<br>Leu | AAA<br>Lys<br>120 | ACA<br>Thr | ACT<br>Thr | 617 |
| TTA<br>Leu | GCT<br>Ala | AAG<br>Lys<br>125 | ACT<br>Thr | ACT<br>Thr | AAA<br>Lys | GAA<br>Glu | AAT<br>Asn<br>130 | GAG<br>Glu | ATT<br>Ile | TCA<br>Ser | GAA<br>Glu | GCT<br>Ala<br>135 | AGC<br>Ser | CGT<br>Arg | AAA<br>Lys | 665 |
| GGG<br>Gly | TTA<br>Leu<br>140 | AGC<br>Ser | CGA<br>Arg | GAC<br>Asp | TTA<br>Leu | GAA<br>Glu<br>145 | GCT<br>Ala | TCT<br>Ser | CGT<br>Arg | ACA<br>Thr | GCT<br>Ala<br>150 | AAA<br>Lys | AAA<br>Lys | GAG<br>Glu | CTA<br>Leu | 713 |
| GAA<br>Glu<br>155 | GCT<br>Ala | AAG<br>Lys | CAT<br>His | CAA<br>Gln | AAA<br>Lys<br>160 | TTA<br>Leu | GAA<br>Glu | GCA<br>Ala | GAA<br>Glu | AAC<br>Asn<br>165 | AAA<br>Lys | AAA<br>Lys | CTA<br>Leu | ACA<br>Thr | GAA<br>Glu<br>170 | 761 |
| GGC<br>Gly | AAT<br>Asn | CAG<br>Gln | GTT<br>Val | TCA<br>Ser<br>175 | GAA<br>Glu | GCT<br>Ala | AGT<br>Ser | CGT<br>Arg | AAA<br>Lys<br>180 | GGT<br>Gly | CTA<br>Leu | AGT<br>Ser | AAC<br>Asn | GAC<br>Asp<br>185 | TTA<br>Leu | 809 |
| GAA<br>Glu | GCT<br>Ala | TCT<br>Ser | CGT<br>Arg<br>190 | GCA<br>Ala | GCT<br>Ala | AAA<br>Lys | AAA<br>Lys | GAA<br>Glu<br>195 | CTA<br>Leu | GAA<br>Glu | GCT<br>Ala | AAG<br>Lys | TAC<br>Tyr<br>200 | CAA<br>Gln | AAA<br>Lys | 857 |
| TTA<br>Leu | GAG<br>Glu | ACT<br>Thr<br>205 | GAT<br>Asp | CAC<br>His | CAA<br>Gln | GCC<br>Ala | CTA<br>Leu<br>210 | GAA<br>Glu | GCT<br>Ala | AAG<br>Lys | CAC<br>His | CAA<br>Gln<br>215 | AAA<br>Lys | TTA<br>Leu | GAG<br>Glu | 905 |
| GCT<br>Ala | GAT<br>Asp<br>220 | TAC<br>Tyr | CAA<br>Gln | GTT<br>Val | TCA<br>Ser | GAG<br>Glu<br>225 | ACT<br>Thr | AGC<br>Ser | CGT<br>Arg | AAG<br>Lys | GGT<br>Gly<br>230 | CTA<br>Leu | AGT<br>Ser | CGT<br>Arg | GAC<br>Asp | 953 |
| CTT<br>Leu<br>235 | GAA<br>Glu | GCG<br>Ala | TCT<br>Ser | CGT<br>Arg | GAA<br>Glu<br>240 | GCT<br>Ala | AAT<br>Asn | AAG<br>Lys | AAG<br>Lys | GTT<br>Val<br>245 | ACA<br>Thr | TCT<br>Ser | GAG<br>Glu | TTA<br>Leu | ACA<br>Thr<br>250 | 1001 |
| CAA<br>Gln | GCA<br>Ala | AAA<br>Lys | GCT<br>Ala | CAA<br>Gln<br>255 | CTC<br>Leu | TCA<br>Ser | GCG<br>Ala | CTT<br>Leu | GAA<br>Glu<br>260 | GAA<br>Glu | AGT<br>Ser | AAG<br>Lys | AAA<br>Lys | TTA<br>Leu<br>265 | TCA<br>Ser | 1049 |
| GAA<br>Glu | AAA<br>Lys | GAA<br>Glu | AAA<br>Lys<br>270 | GCT<br>Ala | GAG<br>Glu | TTA<br>Leu | CAA<br>Gln | GCA<br>Ala<br>275 | AAA<br>Lys | CTA<br>Leu | GAT<br>Asp | GCA<br>Ala | CAA<br>Gln<br>280 | GGA<br>Gly | AAA<br>Lys | 1097 |
| GCC<br>Ala | CTC<br>Leu | AAA<br>Lys<br>285 | GAA<br>Glu | CAA<br>Gln | TTA<br>Leu | GCA<br>Ala | AAA<br>Lys<br>290 | CAA<br>Gln | ACT<br>Thr | GAA<br>Glu | GAG<br>Glu | CTT<br>Leu<br>295 | GCA<br>Ala | AAA<br>Lys | CTA<br>Leu | 1145 |
| AGA<br>Arg | GCT<br>Ala | GAA<br>Glu<br>300 | AAA<br>Lys | GCG<br>Ala | GCA<br>Ala | GGT<br>Gly | TCA<br>Ser<br>305 | AAA<br>Lys | ACA<br>Thr | CCT<br>Pro | GCT<br>Ala | ACC<br>Thr<br>310 | AAA<br>Lys | CCA<br>Pro | GCT<br>Ala | 1193 |
| AAT<br>Asn | AAA<br>Lys | GAA<br>Glu | AGA<br>Arg | TCA<br>Ser | GGT<br>Gly | AGA<br>Arg | GCT<br>Ala | GCT<br>Ala | CAA<br>Gln | ACA<br>Thr | GCT<br>Ala | ACA<br>Thr | AGA<br>Arg | CCT<br>Pro | AGC<br>Ser | 1241 |

| | | | | | | | | | | | | | | | | |
|---|---|---|---|---|---|---|---|---|---|---|---|---|---|---|---|---|
|315| | | | |320| | | | |325| | | | |330| |
|CAA|AAT|AAA|GGA|ATG|AGA|TCA|CAA|TTA|CCG|TCA|ACA|GGC|GAA|GCA|GCT|1289|
|Gln|Asn|Lys|Gly|Met|Arg|Ser|Gln|Leu|Pro|Ser|Thr|Gly|Glu|Ala|Ala| |
| | | | |335| | | |340| | | |345| | | | |
|AAC|CCA|TTC|TTT|ACA|GCA|GCA|GCT|GCA|ACA|GTG|ATG|GTA|TCT|GCT|GGT|1337|
|Asn|Pro|Phe|Phe|Thr|Ala|Ala|Ala|Ala|Thr|Val|Met|Val|Ser|Ala|Gly| |
| | | |350| | | |355| | | |360| | | | | |
|ATG|CTT|GCT|CTA|AAA|CGC|AAA|GAA|GAA|AAC|TAAGTCTTTA|GAACTTGGTT| | | | |1387|
|Met|Leu|Ala|Leu|Lys|Arg|Lys|Glu|Glu|Asn| | | | | | | |
| | |365| | | |370| | | | | | | | | | |

TTTGTAACGG TGCAATAGAC AAAAGCAAGC AAGGCCAAAA ACTGAGAAAG TCCTAAAAAG 1447

CTGGCCTTTA CCCCTAAAAA TTAATGTTTT ATAATAAGA TGTTAGTAAT ATAATTGATA 1507

AATGAGATAC ATTTAATCAT TATGGCAAAA GCAAGAAAAA TAGCTGTATC ATA 1560

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

Ser Ala Gly Met Leu Ala Leu Lys Arg Lys Glu Glu Asn
1          5              10

( 2 ) INFORMATION FOR SEQ ID NO:3:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Met Ala Arg Gln Gln Thr Lys Lys Asn Tyr Ser Leu Arg Lys Leu Lys
1              5                    10                    15

Thr Gly Thr Ala Ser Val Ala Val Ala Leu Thr Val Leu Gly Ala Gly
                 20                         25                      30

Phe Ala Asn Gln Thr Glu Val Arg Ala Asp Glu Ala Lys Lys Met Glu
                 35                         40                          45

Val Lys Glu Ser Glu Lys Glu Ser Gln Tyr Lys Thr Leu Ala Leu Arg
       50                         55                         60

Gly Glu Asn Ala Asp Leu Arg Asn Val Asn Ala Lys Tyr Leu Glu Lys
65                        70                         75                       80

Ile Asn Ala Glu Glu Glu Lys Asn Lys Lys Leu Glu Ala Ile Asn Lys
                         85                         90                         95

Glu Leu Asn Glu Asn Tyr Tyr Lys Leu Gln Asp Gly Ile Asp Ala Leu
                   100                      105                      110

Glu Lys Glu Lys Glu Asp Leu Lys Thr Thr Leu Ala Lys Thr Thr Lys
                   115                      120                      125

Glu Asn Glu Ile Ser Glu Ala Ser Arg Lys Gly Leu Ser Arg Asp Leu
     130                         135                      140

Glu Ala Ser Arg Thr Ala Lys Lys Glu Leu Glu Ala Lys His Gln Lys
145                      150                      155                    160

Leu Glu Ala Glu Asn Lys Lys Leu Thr Glu Gly Asn Gln Val Ser Glu
                   165                      170                      175

Ala Ser Arg Lys Gly Leu Ser Asn Asp Leu Glu Ala Ser Arg Ala Ala
                   180                      185                      190

| Lys | Lys | Glu 195 | Leu | Glu | Ala | Lys 200 | Tyr | Gln | Lys | Leu | Glu 205 | Thr | Asp | His | Gln |

| Ala | Leu 210 | Glu | Ala | Lys | His 215 | Gln | Lys | Leu | Glu | Ala 220 | Asp | Tyr | Gln | Val | Ser |

| Glu 225 | Thr | Ser | Arg | Lys | Gly 230 | Leu | Ser | Arg | Asp | Leu 235 | Glu | Ala | Ser | Arg | Glu 240 |

| Ala | Asn | Lys | Lys | Val 245 | Thr | Ser | Glu | Leu | Thr 250 | Gln | Ala | Lys | Ala | Gln 255 | Leu |

| Ser | Ala | Leu | Glu 260 | Glu | Ser | Lys | Lys | Leu 265 | Ser | Glu | Lys | Glu | Lys 270 | Ala | Glu |

| Leu | Gln | Ala 275 | Lys | Leu | Asp | Ala | Gln 280 | Gly | Lys | Ala | Leu | Lys 285 | Glu | Gln | Leu |

| Ala | Lys 290 | Gln | Thr | Glu | Glu | Leu 295 | Ala | Lys | Leu | Arg | Ala 300 | Glu | Lys | Ala | Ala |

| Gly 305 | Ser | Lys | Thr | Pro | Ala 310 | Thr | Lys | Pro | Ala | Asn 315 | Lys | Glu | Arg | Ser | Gly 320 |

| Arg | Ala | Ala | Gln | Thr 325 | Ala | Thr | Arg | Pro | Ser 330 | Gln | Asn | Lys | Gly | Met 335 | Arg |

| Ser | Gln | Leu | Pro 340 | Ser | Thr | Gly | Glu | Ala 345 | Ala | Asn | Pro | Phe | Phe 350 | Thr | Ala |

| Ala | Ala | Ala 355 | Thr | Val | Met | Val | Ser 360 | Ala | Gly | Met | Leu | Ala 365 | Leu | Lys | Arg |

| Lys | Glu | Glu 370 | Asn |

STREPTOCOCCAL IMMUNOGLOBULIN A BINDING PROTEIN ENCODED BY EMML2.2

This invention concerns a gene coding for a novel immunoglobulin A (IgA) binding protein from group A streptococci of Class II, a process for producing the protein by genetic recombination and the use of the protein to capture and measure IgA.

Nucleotide accession number: the nucleotide sequence encompassing the gene emmL2.2 coding for the IgA binding protein of the present invention is available from EMBL/GenBank/DDJB under accession number X61276. DNA sequence for the polynucleotide coding for protein ML2.2 is submitted on a floppy disk with the present specification.

BACKGROUND OF THE INVENTION

Group A streptococci are responsible for a wide variety of human diseases, the most common of which are nasopharyngitis and impetigo. Nearly all clinical isolates have the antiphagocytic factor, M protein, on their surface. This virulence factor displays extreme antigenic diversity within its amino-terminal region. It is these highly variable portions of M proteins which form the basis of the serological typing scheme which was formulated in the 1930s prior to knowledge of any structural detail (Lancefield, R. C., *J. Immunol.* 89:307–313 (1962)).

In recent years, the sequences of M or M-like proteins have been reported (Frithz, E., Heden, L. O. and Lindahl, G. *Mol. Microbiol.* 3:1111 (1989)). The M-like molecules are structurally similar to M proteins in that they exhibit significant levels of sequence homology; however, they are not considered to be M protein itself because an antiphagocytic property has not been formally demonstrated.

Group A streptococci can be divided into two major classes partly on the basis of their immunoreactivity with a pair of monoclonal antibodies directed to epitopes which lie within the relatively conserved half of M proteins (Bessen, D. and Fischetti, V. A. *J. Exp. Med.* 172:1757 (1990); Bessen, D., Jones, K. F. and Fischetti, V. A. *J. Exp. Med.* 169:269 (1989)). Class I isolates are defined as those binding one or both monoclonal antibodies, whereas class II isolates do not bind either monoclonal antibody. In addition, the classes differ in their ability to exhibit opacity factor activity, and in several pathogenic properties of these organisms (Bessen, D. and Fischetti, V. A. *J. Infect. Dis.* 161:747 (1990)). For example, nearly all serotypes found in association with major outbreaks of rheumatic fever are class I. The classes also differ in ability to bind IgA, with this activity being specific for class II. Obviously this property is important to the function of streptococci as the arp4 protein reported by Lindahl et al. (European Patent Application 367890), e.g., is from class II streptococci and the IgA-binding protein of Russell-Jones et al. (U.S. Pat. No. 4,757,134) is from group B streptococci.

Immunoglobulin A is an important component of the bodily response to pathogens and other disorders. An early mucosal immune response to invasion is production of antibodies of the A class and as a result, elevated levels of IgA can be found in extracts of infected membranes such as saliva, urine, feces and urogenital extracts. Certain disorders such as kidney or liver malfunctions and early cancer detection may also be correlated to IgA. Indeed the human body produces more IgA daily than any other antibody class.

Accordingly, reagents to capture and measure IgA have been sought.

SUMMARY OF THE INVENTION

Two M or M-like protein genes were cloned from a single streptococcus A class II isolate. It was discovered that the product of the downstream gene, hereinafter termed ML2.2, is a protein that exhibits IgA-binding activity (Bessen, D. E. and Fischetti, V. A., *Infection and Immunity* (1992) "Nucleotide Sequence of Two Adjacent M or M-Like Protein Genes of Group A Streptococci: Different RNA Transcript Levels and Identification of a Unique IgA Binding Protein," 60:124–135, herein incorporated by reference). Described here is a novel process for producing high quantities of this IgA binding protein hereinafter referred to as ML2.2.

The polynucleotide of the present invention comprises DNA of approximately 1.6 kb which codes for a polypeptide having the ability to bind IgA. The polypeptide is an approximately 36 to 42 kD protein expressed by a Group A streptococcus of the IIb class, or a fragment or equivalent of the protein. The polynucleotide has the DNA sequence given in FIG. 1. The amino acid sequence of the protein product of the polynucleotide is also given in FIG. 1. Most especially the present invention sets forth the polynucleotide sequence which codes for a polypeptide which binds IgA.

The present invention further concerns a plasmid comprising this polynucleotide sequence, preferably plasmid pML2-14.

According to the process of the subject invention, microorganisms which have been transformed with the gene coding for ML2.2 produce and secrete large quantities of the recombinant protein. Specifically, according to the subject invention, a suitable host, an *Escherichia coli*, for example, can be transformed with 1.6 kb DNA comprising the nucleotide sequence shown in SEQ ID NO. 1. This sequence codes for the IgA binding protein of approximately 42,000 daltons designated ML2.2, whose amino acid sequence is also shown in SEQ ID NOS. 1 and 3.

The product of this process, ML2.2, may be used to detect the presence of IgA in a biological sample. To detect IgA, the sample is contacted with the protein under conditions for suitable for reaction, in the presence of suitable buffers and salts, for example, to bind IgA to the protein and the bound product is observed.

Most preferably the protein of the present invention is affixed to a solid surface, a microtiter plate, for example, or an inert bead such as polystyrene or latex to form an immunoadsorbent for removing IgA from a biological sample. IgA may be removed from a sample by contacting the sample with the immunoadsorbent under conditions which allow IgA to bind to the immunoadsorbent. Microtiter plates, for example, may be coated with the protein or beads may be packed into a column through which sample may be passed.

The present invention also sets forth a process for preparing essentially pure IgA from a biological sample, serum, for example, containing IgA. In this process the sample is then contacted with the immunoadsorbent comprising the protein of the present invention, allowing IgA in the sample to bind to the immunoadsorbent. The bound IgA is washed, preferably with a suitable buffer, to remove associated proteins and other contaminants. Finally IgA itself is eluted from the immunoadsorbent by buffers, electroelution or other method known to the art.

In preferred embodiments of the present invention, the protein is conjugated to a group suitable for being observed. Any such groups known to persons skilled in the art may be used. Enzymes such as alkaline phosphatase or peroxidase, metals such as gold or a member of the biotin-avidin binding pair may be used as labels.

The present invention also sets forth kits comprising immunoadsorbent wherein the protein of the present invention is affixed. Kits may also comprise the protein of the present invention labeled for use as tracers.

DETAILS OF THE INVENTION

Figure 1:
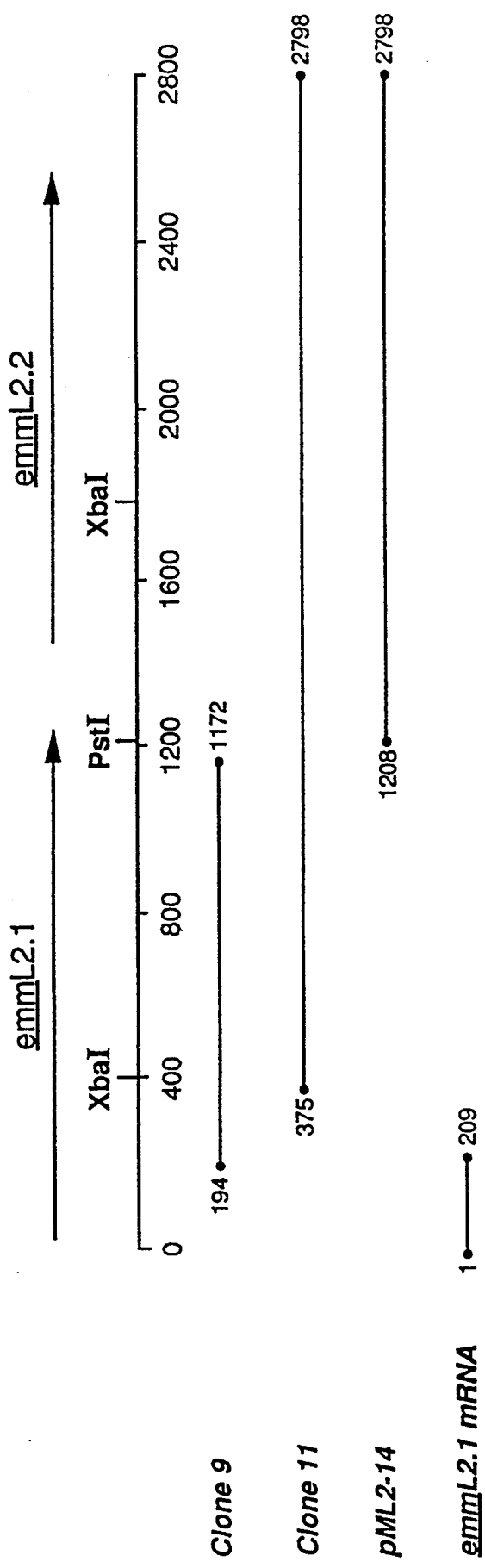
FIG. 1 gives the region of the T2/MR chromosome cloned and sequenced to produce the nucleotide sequence of SEQ ID NO. 1. Arrows indicate the coding regions of emmL2.1 and emmL2.2. Positions of streptococcal DNA that were cloned into the M13mp19 (inserts from clones 9 and 11) and pUC18 (pML2-14) vectors used for sequencing are shown.
Figure 2:
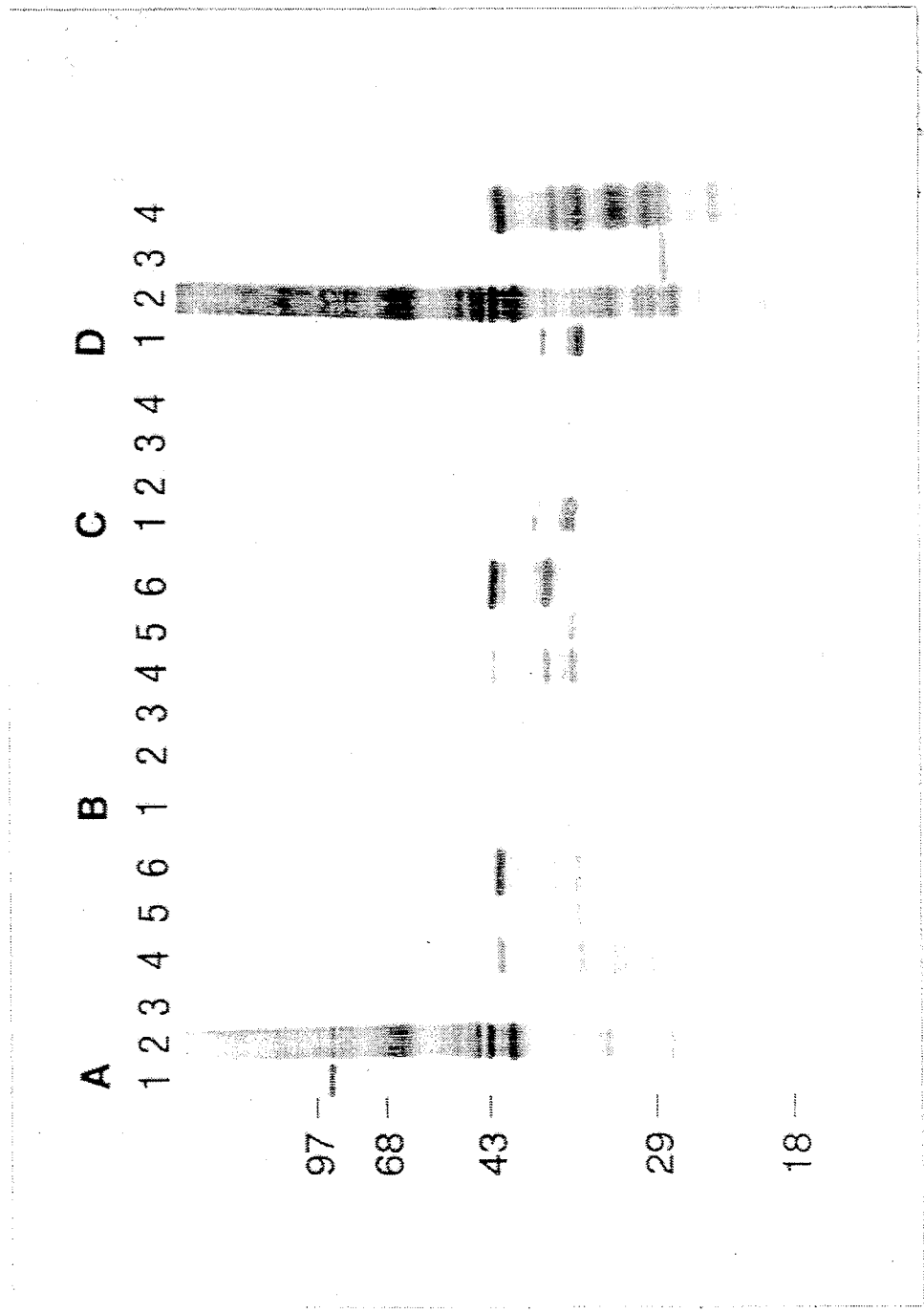
FIG. 2 gives the Western blot analysis of the cloned emmL2.2 gene product. Lanes 1 contain lysin extract of 29452, a streptococcal strain (type 22, class II) obtained from the Institute of Hygiene and Epidemiology, Prague, Czechoslovakia, Lanes 2 contain lysin extract of T2/MR, a M-rich isolate of Group A streptococcal strain T2/44/RB4/119 (Class II) from the Lancefield collection (The Rockefeller University), Lanes 3 contain whole E. coli XL-1 cells and Lanes 4 contain whole E. coli XL-1 cells harboring pML2-14. Blot A is anti-coli6, blot B is human myeloma IgA, blot C is human IgG-Fc fragment and blot D is anti-peptide d240 to 260. The positions of molecular size markers (in kD) are shown to the left.

This invention provides a novel recombinant protein and a novel gene and methods for producing this protein. The novel recombinant protein, and subfragments thereof, have affinity for IgA and can be used in a variety of assays and kits.

One aspect of the subject invention is a gene coding for a recombinant protein. The nucleotide sequence of this gene is shown in SEQ ID NO. 1. SEQ ID NOS. 1 and 3 also show the deduced amino acid sequence of the recombinant protein encoded by the gene shown in SEQ ID NO. 1.

The invention further concerns a recombinant polynucleotide sequence comprising a vector in which a DNA sequence coding for the subject recombinant protein, or a fragment thereof, expressible in a suitable host has been inserted. Thus, said vector encodes the novel IgA binding protein and/or a fragment of this protein with substantially the same binding properties to immunoglobulin A. Specifically, the vector may be chosen from plasmids, phage DNA, or derivatives or fragments thereto, or combinations of plasmids and phage DNA and yeast plasmids.

The invention also concerns a host infected, transformed, or transfected with a recombinant DNA molecule comprising a vector in which a DNA sequence coding for the desired protein, or fragment thereof, expressible is a suitable host has been inserted. The inserted DNA is characterized in that the DNA sequence codes for the recombinant IgA binding protein and/or a fragment of this protein with substantially the same binding properties to immunoglobulin A. Among the many suitable hosts that can be infected, transformed, or transfected with the recombinant DNA molecule according to the invention and thereby express this protein or fragments thereof are gram positive or negative bacteria such as E. coli, Bacillus subtilis, insect cells and yeast cells.

The various methods employed in the preparation of the plasmids and transformation of host organisms are well known in the art. These procedures are all described in Maniatis, T., E. F. Fritsch, and J. Sambrook (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g., E. coli cells, prepare plasmid DNA, electrophorese proteins, and sequence DNA.

The DNA sequence of the subject invention can be most readily obtained by a person skilled in the art by isolating said DNA from Group A streptococcal strain T2/44/RB4/119, the M2 typing strain from the Lancefield collection (The Rockefeller University). The nucleotide sequences disclosed herein can also be prepared by a "gene machine" by procedures well known in the art. This is possible because of the disclosure of the nucleotide sequence.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. The amino acid sequences of the recombinant IgA binding protein and fragments therefore, of the subject invention can be prepared by nucleotide sequences other than that which is shown in SEQ ID NO. 1. Functionally equivalent nucleotide sequences encoding the novel amino acid sequence of these proteins and fragments can be prepared by known synthetic procedures. Accordingly, the subject invention includes such functionally equivalent nucleotide sequences.

Thus the scope of the subject invention includes not only the specific nucleotide sequences depicted herein, but also all equivalent nucleotide sequences coding for molecules with substantially the same antigenic, immunogenic, or therapeutic activity.

Further, the scope of the subject invention is intended to cover not only the specific amino acid sequences disclosed, but also similar sequences of proteins or protein fragments having comparable biological activity.

Preparation of nucleotide. Randomly sheared chromosomal DNA, derived from a low hemolytic colony of strain T2/44/RB4/119 termed T2/MR (type 2, class II) was cloned into lambda gt11 through EcoRI linkers and partially sequenced (2). Plaques were first screened with anti-ColiM6 and then with M2 typing sera. Two clones were obtained: clones 9 and 11. Purified lambda gt11 replicative-form DNA containing inserts were subcloned into both M13mp19 and pUC18 vectors. The insert from clone 11 was subcloned into pUC18 to generate pML2-11. The 1.6 kb PstI-EcoRI fragment derived from pML2-11 was ligated into pUC18 to construct pML2-14.

Purification of polypeptide. Purification of a 34.5 kD fragment of ML2.2, containing IgA-binding activity was performed by growing E. coli containing pML2-14 to mid-log, and preparing a periplasmic fraction. The fraction was dialyzed in buffer containing protease inhibitors and then contacted with MonoQ and washed in 0.05 M Tris (pH 8) containing 0.005 M EDTA. The protein was in fall-through fraction.

The protein was affinity purified with immobilized human myeloma IgA and then eluted with glycine, pH 2.0. The first eluted fractions were re-applied to the column. Eluants were dialyzed and concentrated. Final purification was obtained by contacting eluant with mono-S in 0.05 M NaOAc, pH 5.5 and 0.005 M EDTA. Elution was obtained in buffer containing gradient up to 1.0 M NaCl.

DNA sequencing. Foreign DNA cloned into M13 and pUC vectors was sequenced by the dideoxy-chain termination method. Overlapping inserts were generated in M13mp19 by T4 polymerase digestion. Streptococcal DNA cloned into pUC18 vectors was sequenced because of the inability to clone the sense strand of major portions of insert 11 into M13 bacteriophage. The DNA sequence of pML2-14 is given in SEQ ID NO. 1.

The longest open reading frame for the emmL2.2 gene extends from nucleotide 1452 to 2567. The first 41 amino acids are homologous to signal peptides of other M and M-like proteins (12, 14). Therefore, the mature emmL2.2 gene product is expected to be 331 residues with a predicted molecular weight of 36,769; this size is in reasonable accordance with the 42 kD band expressed by E. coli harboring pML2-14 (FIG. 1, Lanes 4). There is a single region of sequence repeats in the ML2.2 protein, consisting of three 23-residue C repeat segments separated by two spacers (spanning amino acids 90 to 203).

Sequence identities. Amino acids 1 through 71 of the mature ML2.2 protein sequence display only very limited homologies to the ML2.1 protein located upstream or with other M and M-like molecules. According to maximal alignment of sequences by the Protalign algorithm, there is 53% amino acid sequence identity between ML2.1 and ML2.2 proteins, and the homology is located for the most part within their carboxy-terminal two-thirds. ML2.2 protein exhibits 82% homology to the deduced sequence of ennX, an M-protein of unknown function (16) and appears to be transcriptionally silent in streptococci (6). Arp4 and ML2.2, both IgA-binding proteins, are only 56% identical in sequence, despite their similar functions.

Binding properties of ML2.2 protein.

FIG. 3 shows that whole cell lysates of E. coli harboring pML2-14 bind human myeloma IgA by Western blotting (Blot B, Lane 4). The gene product expressed by pML2-14 displayed several bands, many of which are likely degradation products of the major band at 42 kilodalton. Whole E. coli cells having no pML2-14 do not bind IgA. Also the lysin extract of streptococcal strain 29452 does not bind IgA although intact cells do bind IgA.

The emmL2.2 gene product, ML2.2 protein, fails to bind the class I-specific monoclonal antibodies which recognize epitopes in the C repeat regions of class I molecules.

The Ig-binding sites within M and M-like molecules have not been identified. The three M or M-like immunoglobulin binding proteins cloned and sequenced to date (Arp4, ProtH and ML2.2) have in common class II-like C repeat regions (2) and subtleties within the class II C repeat may influence Ig-binding.

---

We claim:

1. An isolated DNA molecule of DNA encoding the protein represented by SEQ ID NO. 3.
2. A DNA molecule, according to claim 1, wherein said molecule is represented by SEQ ID NO. 1.
3. A recombinantly produced plasmid comprising DNA represented by SEQ ID NO. 1.
4. A plasmid according to claim 3, wherein said plasmid is pML2-14.
5. A cell in culture transformed with the DNA of claim 1.
6. A cell according to claim 5, wherein said cell is *Escherichia coli.*
7. A process for preparing an IgA-binding polypeptide comprising
   cultivating the transformed cell of claim 5 under conditions such that said polypeptide is expressed, and
   recovering said polypeptide from the culture.

* * * * *

UNITED STATES PATENT AND TRADEMARK OFFICE
CERTIFICATE OF CORRECTION

PATENT NO. : 5,352,588
DATED : October 4, 1994
INVENTOR(S) : Fischetti et al.

It is certified that error appears in the above-indentified patent and that said Letters Patent is hereby corrected as shown below:

Column 2, line 28: Delete "FIG. 1" and insert --SEQ ID NO. 1--

Column 3, line 7: Delete "the an may be used." and insert --the art may be used.--

Signed and Sealed this

Seventh Day of February, 1995

Attest:

BRUCE LEHMAN

*Attesting Officer*    *Commissioner of Patents and Trademarks*